United States Patent [19]
Lee

[11] Patent Number: 5,831,725
[45] Date of Patent: Nov. 3, 1998

[54] TWO-MODE SURFACE DEFECT TESTING SYSTEM

[75] Inventor: Frederick H. Lee, Plantation, Fla.

[73] Assignee: Atlas Electric Devices Co., Chicago, Ill.

[21] Appl. No.: 732,063

[22] Filed: Oct. 16, 1996

[51] Int. Cl.$^6$ .................................................. G01N 21/47
[52] U.S. Cl. ......................................... 356/237; 356/446
[58] Field of Search .................................. 356/237, 236, 356/446

[56] References Cited

U.S. PATENT DOCUMENTS

| | | | |
|---|---|---|---|
| 4,861,164 | 8/1989 | West | 356/446 |
| 5,068,739 | 11/1991 | Filo | 356/236 |
| 5,155,558 | 10/1992 | Tannenbaum et al. | 356/446 |
| 5,406,367 | 4/1995 | Sopori | 356/237 |
| 5,461,416 | 10/1995 | Bettinardi | 348/62 |
| 5,497,234 | 3/1996 | Haga | 356/237 |

OTHER PUBLICATIONS

Brochure by Northeast Robotics, Inc. entitled: State of the Art Machine Vision Illumination, copyright 1994.
Brochure entitled Integrating Sphere Systems by labsphere of North Sutton, New Hampshire (undated).
Selected pages from the general catagogue of The Integrated Solutions Company, copyright 1994, including the cover and pp. 7–14.

*Primary Examiner*—Frank G. Font
*Assistant Examiner*—Zandra V. Smith
*Attorney, Agent, or Firm*—Gerstman, Ellis & McMillin, Ltd.

[57] ABSTRACT

A two-mode surface defect testing device comprises a first source of substantially collimated light which passes along a first light path system to direct the collimated light to a holder for a surface for testing. The surface reflects the light, which is received and directed from the surface typically through at least some of the first light path system to an image processing apparatus. A second source of light is also provided, for providing substantially non-collimated light from the second source to a surface for testing in the holder, which may be the same surface for testing as above. This non-collimated light is reflected from the surface to image processing apparatus. The light may be non-polarized. By use of the two modes of testing, defects may be respectively detected at the outer surface of a transparent coating over an opaque surface, and defects in the opaque surface itself may also be detected.

33 Claims, 2 Drawing Sheets

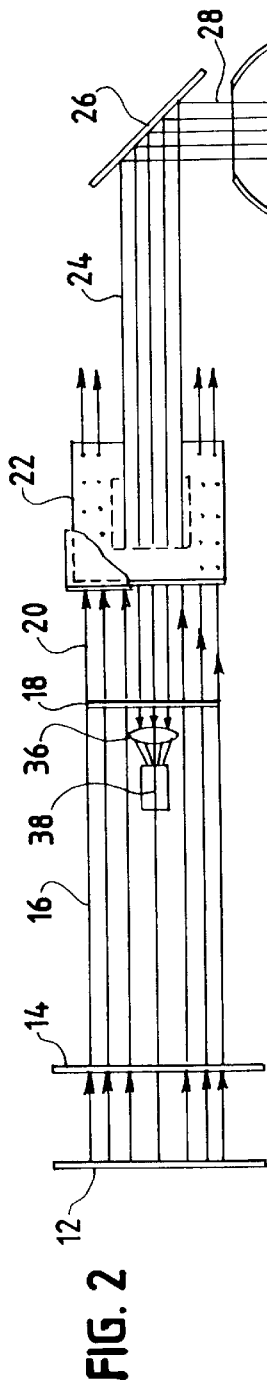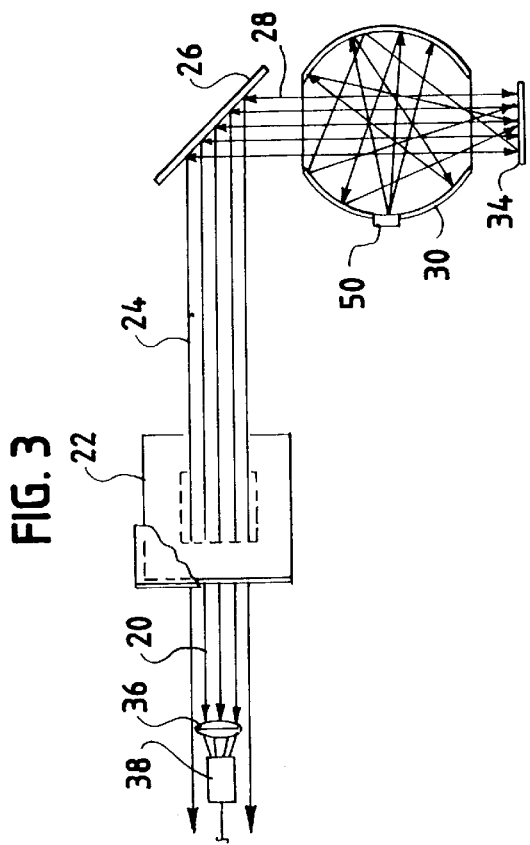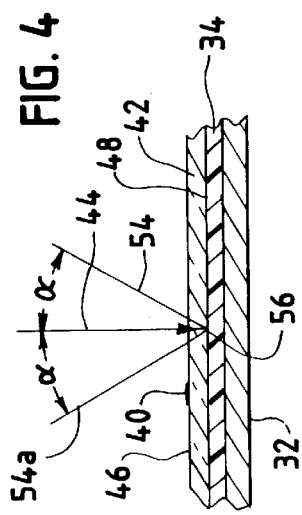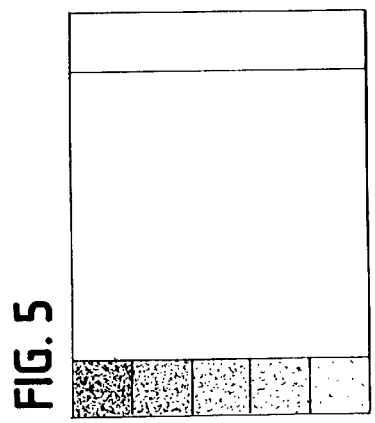

TWO-MODE SURFACE DEFECT TESTING SYSTEM

BACKGROUND OF THE INVENTION

Fine surfaces such as the finished surfaces of new automobiles, and other surfaces, need to be carefully monitored for defects which may not be readily visible with a quick look, but which may be later seen by the users as a defect in the finish of the surface. Currently, light inspection systems of such surfaces use polarized light and a lens. Such a system looks primarily at the outermost surface only, and misses defects which may be found on a colored surface which is covered with transparent coating, as may be the case in some automotive finishes and in other fine, decorative surfaces.

By this invention, a surface defect testing system is provided which may detect defects either on a basic, colored surface, or on the surface of a transparent coating which covers the colored surface. The apparatus of this invention may operate in two different modes, to test the same sample in two different ways in order to determine the presence or absence of defects both on the basic, colored surface and/or on the exposed surface of an outer transparent coating over the colored surface. Defect detection may be automated if desired, or performed by simple, visual inspection making use of the apparatus, so that continuous, routine testing of the finish of automotive surfaces and other fine surfaces may be accomplished without the need for polarized light.

DESCRIPTION OF THE INVENTION

By this invention, a two-mode surface defect testing system is provided. The system comprises a first source of substantially collimated light, i.e., light that is substantially parallel in its direction of travel, which light may be produced by spacing the light source by at least about 16 inches from the surface being tested.

A first light path system is provided, to direct the collimated light to a holder of a surface for testing. The first light path system also is for receiving and directing reflected light from the surface for testing in the holder, rearwardly again through at least some of the first light path system, to an image processing apparatus, which may be simply a lens for optical viewing, a charge coupled diode (ccd) camera, a video camera, a film camera, or the like. The surface being tested is placed essentially perpendicular to the collimated light that strikes it.

A second source of light is also provided with a second light path system for passing and typically reflecting substantially non-collimated light from the second source onto a surface for testing in the holder, which may be the same surface as described above if desired. This non-collimated light may also be reflected through at least part of the first light path system to the image processing apparatus. "Non-collimated" is a term that broadly describes non-directional, substantially non-parallel, or diffused light.

Thus, two alternative modes of light testing are provided: one with collimated light, and the other with non-collimated light. It has been found that the collimated light is capable of detecting defects on specular (shiny) surfaces such as the outer, smooth surface of a transparent coating over an opaque surface, such as a clear, outer coating of an automotive finish. What is seen in this mode from such a surface is an uniform, bright field with reflective surface defects showing up as darker marks or blemishes.

This mode of testing tends not to see blemishes which are under the outer, reflective surface of a clear coating.

When the second mode of the apparatus of this invention is used, the non-collimated light tends to detect defects that are below the transparent outer layer in a dark background, particularly those defects in a dark-colored, opaque surface which is coated by, a transparent layer. Also, this latter mode of light testing with non-collimated light can detect defects on a matte surface which may or may not be coated with a transparent layer. In this mode of operation, a darker field is seen, with any defects appearing as bright markings. Typically the field in either mode of use can have dimensions of ½ inch by ½ inch. Also, the true color of the colored surface under the transparent surface can be accurately monitored in this mode.

Accordingly, a complete surface analysis can be made by this invention of a single sample, so that defects may be noted on an outer surface of a transparent coating, and other defects may be noted on the interior, opaque background surface that carries the transparent surface, for a complete analysis of defects in the whole surface. Also, the respective modes of an apparatus may be used separately. The first, collimated mode may be used to determine defects on a reflective surface, while the second, non-collimated analysis mode may be used to monitor particularly the true color of a non-reflective surface, along with defect monitoring. In the second, non-collimated analysis mode, defects on a dark-colored surface with a transparent coating can be seen. All defects may show up. However, the defects on the outer surface of the transparent coating can be identified since they also show up in the collimated light mode analysis technique, while deep defects under a transparent coating are less likely to be seen in that first mode. Thus, one can determine the location of the defects, whether on the outer transparent surface, or on the inner, colored surface by analyzing the surface using both modes, particularly when the colored, undersurface is of a darker color.

Thus, the present invention provides a highly useful analytical tool, which typically may operate with non-polarized light, although it may be used with polarized light if desired. Also, both types of light may be simultaneously used. In this circumstance, the non-collimated-light can "wash out" some of the sensitivity of the collimated light, so that only larger, deeper defects are noted, while small defects are no longer seen. Thus, statistical studies can be accomplished as to the size distribution of defects on the outer surface of particularly a transparent-coated surface.

The second light path system typically comprises a substantially spherical, internally reflective surface, open at the top and bottom, with the second light source mounted relatively closely to the side of the reflective surface to pass light into the spherical surface. Such a spherical, reflective surface is known to the art as an "integrating sphere", and it provides a source of highly and uniformly non-collimated light out of an opening of the sphere, which may be directed at the holder for the surfaces that are to be tested.

It is also preferred for the testing system of this invention to have a target of known light absorbance, which may be positioned adjacent the surface for testing. Since the target is of known light absorbance, it becomes possible for the intensity of one or both of the light sources to be calibrated by observation of light reflected from the target. Preferably, a pair of targets are positioned adjacent the surface for testing, one of the targets being specifically adapted to calibrate the collimated light and the other of the targets being specifically adapted to calibrate the non-collimated light. An electronic feedback circuit can be provided so that the light emitted from one or both of the light sources can be of a controlled intensity as a function of the observation of the light reflected from the target. Thus, it becomes possible to duplicate analytical work with the system of this invention, duplicating the lighting conditions previously used, or intended for use in the future, in a quantitative manner, so that data taken over the years can be more comparable to each other since known or constant light levels may be used for the work.

One of the pair of targets may preferably comprise a partially light absorbent plate faced at an acute angle to the collimated light, and backed by a mirror surface which is perpendicular to the collimated light. This arrangement is particularly effective for the calibration of collimated light.

Another of the pair of targets used may comprise a partially light-absorbent plate which is backed by a reflective, light scattering surface, typically a highly reflective, white surface. Preferably, both the light absorbent plate and the reflective surface are substantially perpendicular to the general direction of the incident light being measured. This system is effective for calibration of the non-collimated light.

Preferably, the targets comprise separate regions of differing, known light absorbency. Such devices are known as step linear density filters, and are available, for example, from the Reynard Corporation of San Clemente, Calif.

Also the testing system of this invention preferably has the first and second light sources respectively connected to a system for controlling light intensity emitted by the sources in a manner responsive to the intensity of light reflected to the imaging apparatus described above from at least one of the targets present. Thus a reliable, predetermined light intensity is provided.

DESCRIPTION OF THE DRAWINGS

In the drawings.

FIG. 2 is a simplified, elevational view of the apparatus of FIG. 1, shown in its mode in which collimated light is used;

FIG. 3 is a simplified, elevational view of the apparatus of FIG. 1, showing use of the apparatus in its non-collimated light mode;

FIG. 4 is an enlarged, fragmentary, longitudinal sectional view showing how the non-collimated light mode can operate to create a lighted image where a defect resides; and FIG. 5 is a plan view of the area of the holder, target sample, and the light intensity calibrators.

DESCRIPTION OF SPECIFIC EMBODIMENT

Figure 1:
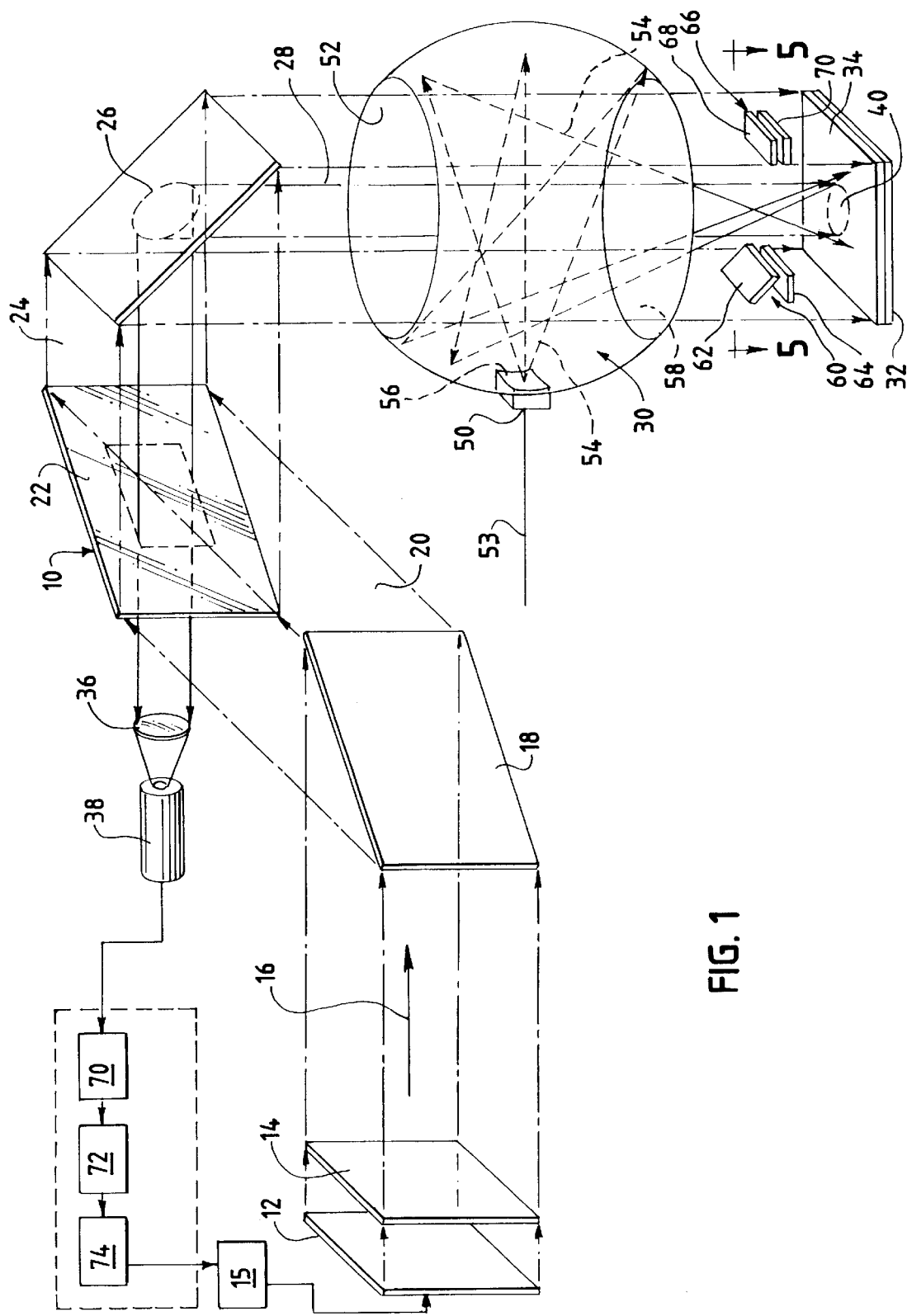
FIG. 1 is a simplified, perspective view of the apparatus of this invention showing the operative parts.

Referring to the drawings, the two-mode surface defect testing system of this invention is, disclosed. The drawings show only the operative parts of the system, with necessary structural framework being omitted. This structural framework may be of any desired conventional design for holding the various components in their positions to control the light beams in the manner described.

Apparatus 10 comprises a first source of light 12, which may comprise sixteen 4×4 branch fiber optic light guide conduits mounted behind a pane of optical diffusing glass 14, as shown, each being connected to a light 15, so that light beams 16 are uniform and free of dark areas across the width thereof. The light beams 16 from first light source 12 strikes angled full-reflecting mirror 18, to be deflected at an angle so that the reflected light path 20 strikes an angled, beam-splitting mirror 22, which may typically may have properties of 50% reflection and 50% transmission. The small rectangle shown on mirror 22 is symbolic to imply the beam splitting characteristic.

The reflected light 24 from the angled, beam splitting mirror 22 strikes another angled, full-reflecting mirror 26, causing reflected light 28 to pass through integrating sphere 30 without reflection therein, to fall upon a holder 32 of any desired design to carry surface for testing 34. By the time that the light has passed through beam portions 16, 20, 24, and 28, it has achieved a substantially collimated characteristic, because the distance that it has traveled is preferably about 20 inches or more, thus being a beam of light which may be about 4 inches square and substantially collimated. Thus the entire surface of the sample to be tested 34 is illuminated with perpendicular, collimated light.

The reflective surface of sample 34 reflects a light beam back through pathway 28, mirror 26, and light pathway 24. Upon striking the beam splitting mirror 22, a portion of the light passes through mirror 22 to lens 36, thus projecting a focused image to ccd camera 38. This image may be stored electronically or in any other desired manner, or the image from lens 36 may be observed visually if desired. Any defect 40 on the highly reflective surface 46 (FIG. 4) will show up as a dark marking in the image seen by ccd camera 38, which image will provide a bright background for that dark marking. This system sees defects on specular, reflective surfaces, which may be a specular surface per se, or may be the outer surface of a transparent coating over a colored, opaque surface, with the defects 40 which are seen being on the outer surface of the transparent coating.

Specifically in FIG. 4, the sample 34 to be analyzed rests upon holder 32 and carries a transparent coating 42. A collimated light beam 44 is shown to fall on reflective outer surface 46 of the transparent coating 42 in perpendicular manner. If the surface is reflective and smooth, each of the collimated light beams 44 will be reflected back in perpendicular manner. If a defect is present, a particular collimated light beam 44 will not to be reflected at an angle perpendicular to surface 46, so the beam is lost, and a resulting dark marking is seen through lens 36.

This mode of operation is shown in FIG. 2. Light source 50 may be off in this mode.

On the other hand, if it is desired to check for defects on a non-reflective surface, particularly, for defects at surface 48 (FIG. 4) which is covered by transparent coating 42, one can activate second light source 50, which is carried on the exterior surface of a sphere 30 having an internal reflective surface 52. This is known as an integrating sphere, the interior of which is typically coated with a highly reflective, white coating. Typically, first light source 12, 15 is shut off.

Second light source 50 may be a point source of light if desired, or a wider source. The light beams 54 enter the interior of integrating sphere 36 through an aperture 56, and bounce in many directions off of the reflective inner wall 52 of the integrating sphere. Light beams thus pass out of bottom aperture 58 of integrating sphere 30 in a large variety of directions, being largely non-parallel to, the axis of integrating sphere 30 and light path 28. This light 54 falls upon the surface 34 to be tested at a variety of angles α (FIG. 4) to the axial direction 44, one of such angled light beams 54 being shown in FIG. 4, along with the same light beam 54a after reflection,.

Much of incoming light beams 54 pass through transparent layer 42, and are reflected at colored, opaque surface 48. The normal situation, when surface 48 is flat and flawless, is for little of the reflected light 54a to reflect along axis 44 and to get back up light paths 28 and 24 to partially reflective mirror 22, so that a fairly dark image is seen through lens 36 in this mode of operation. However, if a defect 56 is found in surface 48, the incoming light 54 from various angles will be reflected in an irregular variety of directions, which will include the direction of axis 44. Thus, defects 56 will reflect light up light passages 28, 24 and through the partially reflective mirror 22, to appear as a brighter image on a darker background through lens 36.

With highly diffused light provided, the pigmented layer (or matte surface without clear medium) is illuminated to bring out its true color information. In other words, the surface will react to the illumination. For example, if a sample contains dark or black color, most of the light will be absorbed. If a sample contains light or white color, most of the light will be reflected. Therefore, in this mode most of the chromatic color related information from the layer is revealed at its fullest with highly diffused light revealing defects or foreign particles which may contain different color information. By this system, defects on outer surface 46 may also be seen against a darker background.

This mode of operation is as illustrated in FIG. 3, and is the opposite of the other mode of operation (FIG. 2) for defects of specular or shiny surfaces 46, which show up as dark markings against a bright background.

Thus, by this invention, surface defects on specular surfaces 46, which may be on transparent layers, may be selectively identified, as distinguished from surface defects on a colored, opaque surface 48, which later defects may also be identified. This all can take place in the same apparatus, consecutively, for testing the same surface, simply by selectively turning the respective light sources 15, 50 on and off.

It is desirable to calibrate the intensity of the light beams that fall upon sample 34, since the intensity of the light sensed by CCD camera 38 is of course strongly related to the intensity of the light emitted through light sources 15 and 50.

Accordingly, a light intensity sensing arrangement may be provided to quantify the intensity of the light that strikes sample 34. With this quantitative data, the lighting conditions can be duplicated at a subsequent time, so that the data obtained can be compared with previously obtained data, or with future data, since the intensity of the light is known.

A first target 60 of known light absorbance is positioned adjacent the sample, surface for testing 34. First target 60 comprises a partially light absorbent plate 62, which is faced at an acute angle (typically about 10 to 40°) to the collimated light 28 coming from light source 12, when the system is being used in the collimated light mode. Light absorbent plate 62 may comprises a step linear density filter from the Reynard Corporation, comprising a glass substrate with a spectrally flat neutral density metallic coating, having density variations that take place in discrete steps. Thus, data may be obtained from any of a variety of varying densities of the filter, as is most appropriate for the particular light and the intensity used.

A mirror 64 is spaced behind light filter 62 so that the light is reflected twice through the filter. Light filter 62 is placed at an angle to deflect off of the axis of light beams 28 any reflected light coming from the surfaces of light filter 62. Light filter 62 and mirror 64 are placed off to one side of the light beams 28, so as to not interfere with the light irradiation of sample 34. Alternatively, the system of filter 62 and mirror 64 may swing into the path of light beams 28 for calibration purposes, and then swing outwardly again for use in the analysis of samples 34.

Light beams 28 pass through filter 62, and are reflected back again through filter 62 in an axial manner, since mirror 64 is positioned perpendicular to light beams 28. Thus, the filtered light beams are reflected back by mirror 26 and beam splitting mirror 22 to CCD camera 38. Since the light absorption of a given region of filter 62 is known, the light intensity emitted by light source 12 can be quantified and the data stored can be compared with data taken at other times.

Then, when it is desired to obtain more data of a type which is comparable to the data previously obtained at such a light intensity, the intensity of light source 12 may be set at the original intensity of the light 15 to provide comparable data.

Second target 66 comprises a second light absorbent plate or neutral density light filter 68 which may be an identical product to filter 62, except that filter 68 is typically positioned with major faces perpendicular to light beams 28. Light filter 68 is backed by a spaced, light colored, (typically white) highly reflective backing 70.

By this means, the intensity of the non-collimated light 54 may be calibrated. The non-collimated light passes through filter 68 from a variety of directions and is further diffused by white backing 70, and passes again through filter 68 upwardly through integrating sphere 30 and up to reflecting mirror 26 and through partially reflecting mirror 22, to be sensed by CCD camera 38. Here also, the intensity of the light source 50 may be quantified so that particular experimental conditions may be repeated using a light source of the same light intensity as in previous runs, so that data from various runs taken at different times may be comparable.

This process of quantification of the light sources may be performed in an automatic manner if desired. Also, the light source intensity may be stabilized at a particular, predetermined value if desired.

This may be accomplished by feeding signals from CCD camera 38 to a conventional imaging board 70 which, in turn, feeds signals to imaging processing/analysis software 72 of a type which is readily adaptable for use in this invention. Analogue/digital input output board 74 is accordingly controlled by the image processing software 72 to control the intensity of light 15 as a function of the signals received from CCD camera 38, and as a further function of the desired intensity of the light 15 stored in memory.

Likewise, light source 50 is connected by wire 53 to input output board 74, so that the intensity of light 50 can be controlled in similar manner in accordance with desired parameters stored in memory.

Thus, a two-mode surface defect testing system is provided which can detect surface defects both on a surface and under a transparent surface, and which can determine the location of the defects respectively on or under a transparent surface. Also, the system may be calibrated for light intensity, automatically if desired, so that sequential batches of data taken over months and years can be comparable. This can all be accomplished with non-polarized light if desired.

The above has been offered for illustrative purposes only, and is not to intended to limit the scope of the invention of this application, which is as defined in the claims below.

What is claimed:

1. A two-mode surface defect testing system which comprises:
   a first source of light;
   a first light path system having a length sufficient to substantially collimate said light and to direct said collimated light to a holder of a surface for testing, and to receive and direct reflected light from said surface to an imaging apparatus, said first light path system being free of collimating lenses;

a second source of light; and a second light path system for providing substantially non-collimated light from said second source onto a surface for testing in said holder, to reflect said non-collimated light to said imaging apparatus.

2. The testing system of claim 1 in which said imaging apparatus is a ccd camera.

3. The testing system of claim 1 in which said light is nonpolarized.

4. The testing system of claim 1 in which said second light path system comprises a substantially spherical reflective surface.

5. The testing system of claim 4 in which the spherical surface has an entry port and an exit port positioned co-axially to allow a linear optical path therethrough.

6. The testing system of claim 1 in which a partially light-reflective, partially light-transparent mirror is positioned in said first light path system to direct light traveling in one direction to travel through the first light path system, and also to permit light traveling in the other direction to pass through said mirror onto a different light path.

7. The surface defect testing system of claim 1 in which said first light path system has a length of at least about 16 inches.

8. The testing system of claim 1 in which said light from said first source passes through a diffuser plate and is uniform and free of dark areas across its width.

9. The testing system of claim 1 in which light from said first source of light which is reflected from said surface is directed to pass through at least of some said first light path system.

10. The testing system of claim 1 in which light from said second source of light which is reflected from said surface is directed to pass through at least of some said first light path system.

11. The testing system of claim 1 in which a target of known light absorbance is positioned adjacent said surface for testing, whereby the intensity of at least one of said light sources can be calibrated by observation of light reflected from said target.

12. The testing system of claim 11 in which said first and second light sources are respectively connected to a system for controlling light intensity emitted by said sources in a manner responsive to the intensity of light reflected to the imaging apparatus from said target.

13. The testing system of claim 12 in which a partially light-reflective, partially light-transparent mirror is positioned in said first light path system to direct light travelling in one direction to travel through the first light path system, and also to permit light travelling in the other direction to pass through said mirror onto a different light path.

14. The testing system of claim 13 in which light from said second source of light which is reflected from said surface is directed to pass through at least some of said first light path system.

15. The testing system of claim 11 in which a pair of said targets are positioned adjacent said surface, the other of said pair of targets comprising a partially light absorbent plate backed by a reflective, light scattering surface for calibrating of non-collimated light.

16. The testing system of claim 15 in which said light source is respectively connected to a system for controlling light intensity emitted by said source in a manner responsive to the intensity of light reflected to the imaging apparatus from at least one of said targets.

17. The testing system of claim 11 in which a pair of said targets are positioned adjacent said surface.

18. The testing system of claim 17 in which one of said pair of targets comprises a partially light absorbent plate faced at an acute angle to said collimated light and backed by a mirror surface perpendicular to said collimated light.

19. The testing system of claim 18 in which the other of said pair of targets comprises a partially light absorbent plate backed by a reflective, light scattering surface.

20. The testing system of claim 19 in which said targets comprise separate regions of differing, known, light absorbance.

21. The testing system of claim 20 in which said first and second light sources are respectively connected to a system for controlling light intensity emitted by said sources in a manner responsive to the intensity of light reflected to the imaging apparatus from at least one of said targets.

22. A surface defect testing system which comprises:

a source of substantially collimated light;

a light path system to direct said collimated light to a holder of a surface for testing and to receive and direct reflected light from said surface to an imaging apparatus; and a target of known light absorbance positioned adjacent the surface for testing, whereby the intensity of said light source can be calibrated by observation of light reflected from said target.

23. The testing system of claim 22 in which said target comprises a partially light absorbent plate faced at an acute angle to the axis of collimated light striking said surface for testing, said plate being backed by a mirror surface perpendicular to said collimated, light.

24. A two-mode surface defect testing system, which comprises:

a first source of light;

a first light path system having a length sufficient to substantially collimate said light and to direct said collimated light to a holder for a surface for testing and to receive and direct reflected light from said surface through at least some of said first light path system to a ccd camera, said first light path system being free of collimating lenses;

a second source of light; and a second light path system for reflecting substantially non-collimated light from said second source onto a surface for testing in said holder, to reflect said non-collimated light through at least part of said first light path system to said ccd camera.

25. The testing system of claim 24 in which said light is nonpolarized.

26. The testing system of claim 25 in which a partially light reflective-partially light transmitting mirror is positioned in said first light path system to direct light traveling in one direction to travel through the first light path system, and also to permit light traveling in the other direction to pass through said mirror onto a different light path.

27. The surface defect testing system of claim 25 in which said first light path system has a length of at least about 16 inches.

28. The testing system of claim 27 in which said first source of substantially collimated light is diffused over an area of at least about 4 square inches.

29. The testing system of claim 28 in which said second light path system comprises a substantially spherical surface coated with a highly reflective white coating and having coaxial entry and exit ports to allow a linear optical path therethrough.

30. The testing system of claim 24 in which said light from said first source passes through a diffuser plate and is uniform and free of dark areas across its width.

31. The method of defect testing a surface which comprises an opaque layer with an overlying transparent layer, said method comprising the following sequential steps in any order:

(1) directing a beam of collimated light to said surface for testing without the use of collimating lenses, and directing reflected light from said surface to an image processing apparatus; and (2) directing a beam of substantially non-collimated light to said surface for testing, and directing reflected light from said surface for testing to said image processing apparatus.

32. The method of claim 31 in which said collimated light falls on said surface in perpendicular manner.

33. The method of claim 31 in which said beam of collimated light is directed to said surface for testing without the use of a collimating lens.

* * * * *